United States Patent [19]

Mooradian

[11] 4,416,542

[45] Nov. 22, 1983

[54] NIGHTTIME/DAYTIME DIFFUSE ATTENUATION COEFFICIENT DEVICE FOR SEAWATER

[75] Inventor: Gregory C. Mooradian, Del Mar, Calif.

[73] Assignee: The United States of America as represented by the Secretary of the Navy, Washington, D.C.

[21] Appl. No.: 273,785

[22] Filed: Jun. 15, 1981

[51] Int. Cl.³ .......................................... G01N 21/17
[52] U.S. Cl. .................................. 356/435; 250/573; 356/442
[58] Field of Search ............... 356/435, 436, 441, 442; 250/573, 574, 575

[56] References Cited

U.S. PATENT DOCUMENTS

| | | | |
|---|---|---|---|
| 3,619,624 | 11/1971 | Sorenson | 356/435 |
| 4,037,973 | 7/1977 | Carr | 356/435 |
| 4,290,695 | 9/1981 | Schmitt | 356/442 |

OTHER PUBLICATIONS

"An Instrument for the Measurement of Spectral Attenuation Coefficient and Narrow Angle Volume Scattering Function of Ocean Waters", Austin et al., SPIE, vol. 64, (1975), Ocean Optics, pp. 50-61.

Primary Examiner—Vincent P. McGraw
Attorney, Agent, or Firm—Robert F. Beers; Ervin F. Johnston; Thomas G. Keough

[57] ABSTRACT

An apparatus and method for measuring the diffuse absorption coefficient of seawater provides reliable readings. An emitter of pulsed light is disposed below the water's surface and an irradiance receiver is located between the pulsed light emitter and the water's surface. Because the irradiance receiver is facing downward, is separated from the light emitter a given amount and may be disposed a suitable distance below the water's surface, reliable day and nighttime readings are obtained that are unaffected by atmospheric or surface conditions.

10 Claims, 1 Drawing Figure

U.S. Patent   Nov. 22, 1983   4,416,542
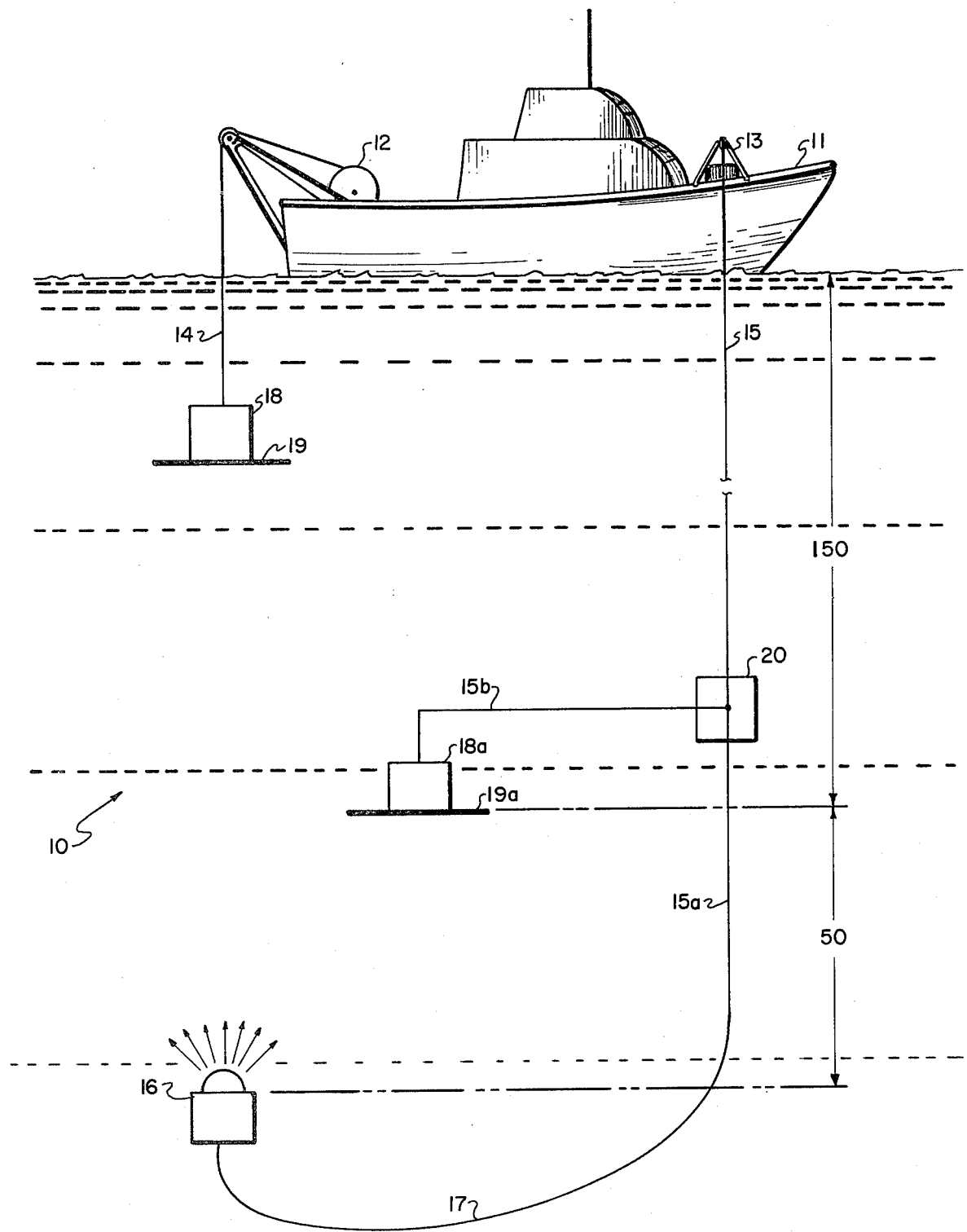

NIGHTTIME/DAYTIME DIFFUSE ATTENUATION COEFFICIENT DEVICE FOR SEAWATER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The increasing interest in developing ocean technologies requires a more thorough understanding of the ocean's properties and its characteristics. Recently, because of a number of inherent advantages, the optical transmission of information through the ocean medium has received a good deal of attention. However, several factors must be taken into consideration. Although a variety of factors influence the quality and reliability of such communications, one that is of particular interest is knowing the diffuse attenuation coefficient K. This coefficient is used to describe the attenuation of downwelling irradiance as a function of depth in natural waters and is an apparent optical property. It is a function of the geometry of measurement and other factors which alter the irradiance distribution as a function of depth.

A thorough explanation and analysis of the diffuse attenuation coefficient parameter is covered in an article by K. S. Baker and R. C. Smith entitled "Quasi-Inherent Characteristics of the Diffuse Attenuation Coefficient for Irradiance" appearing in the Ocean Optics No. 4 issue of the Society of the Photo-Optical Instrumentation Engineers (1979). Definitions, applications and a somewhat extensive idealized data gathering scheme are dealt with in the article and limitations in the approach are listed.

Since the diffuse attenuation coefficient is an apparent optical property, its behavior with depth exhibits reproducible regularities in a wide range of natural water types and it is possible to formulate exact mathematical interrelationships between it and the inherent optical properties. As a consequence, knowing the diffuse attenuation coefficient permits practical solutions to a wide range of problems in ocean optics.

The data obtained by Baker and Smith was gathered under almost ideal environmental and experimental conditions. First, the atmospheric conditions had to remain uniform throughout the data gathering period (all day) and, secondly, the air-water interface had to be relatively smooth for waves increase the uncertainty in measuring depths accurately and require longer integration times to obtain average irradiance values at each depth; the latter is an important factor if complete spectral and depth data are to be obtained throughout the day as a function of the sun angle to the surface. Third, the water column had to be relatively uniform and remain so throughout the duration of the experiment. And lastly, favorable experimental conditions had to be maintained all day to allow accurate data gathering, that is, all instrumentation must remain functional on a moored barge positioned on station. Although the barge provided a stable platform for rapid, efficient and continuous monitoring by several instruments, its shadow compromised the measurements at high noon.

From the foregoing it is apparent that determination of the diffuse attenuation coefficient depends on sea state, wind state, atmospheric conditions, a stable support platform (nonshadowing) as well as availability of numerous instruments and trained operating personnel. Ideal environmental and experimental conditions must coincide. Unfortunately, this highly desirable situation is not as frequent as experimenters would like.

Thus, there is a continuing need in the state-of-the-art for a diffuse attenuation coefficient measuring device which is capable of reliably providing the needed information under a variety of conditions and during the daytime and nighttime.

SUMMARY OF THE INVENTION

The present invention is directed to providing an apparatus and method for measuring the diffuse attenuation coefficient of seawater during both day and night. A pulsed light emitter is disposed below the water's surface and an irradiance receiver is interposed between the pulsed light emitter and the water's surface and facing downward to receive emitted light pulses and generate responsive signals. Lines and winches either suspend or buoy the pulsed light emitter and the irradiance receiver at preselected depths and at predetermined separations to enable an accurate reliable determination of the diffuse attenuation coefficient.

It is a prime object of the invention to provide an improved method and means for determining the diffuse attenuation coefficient.

Yet another object is to provide a method and apparatus for determining the diffuse attenuation coefficient having the receiver looking downwardly to allow an enhanced operation during both daytime and nighttime.

Another object is to provide a method and means for giving a true diffuse attenuation coefficient reading by locating a transmitter and receiver of optical pulses several scattering lengths below a maximum depth of interest to allow diffusing out of the source.

Still another object is to provide a method and apparatus that is cheap and reliable which uses an incoherent pulsed light source that produces high energy pulses.

Yet another object is to provide a method and apparatus not requiring any special pointing by the transmitter of the downwardly facing receiver.

A further object is to provide a diffuse attenuation coefficient determination employing a number of receivers at different depths.

Another object is to provide more than one spaced apart downwardly facing receiver and a pulsed light source for determining the diffuse attenuation coefficient.

Still another object is to provide a method and apparatus that does not obscure a field of view which might otherwise be caused when an upwardly facing receiver is employed.

Still another object is to provide a method and apparatus which reduces the effects of the air-sea interface.

Another object is to provide means for lowering and separating the receivers and a pulsed light source that can determine the diffuse attenuation coefficient irrespective of light intensity changes in the source.

Still another object is to provide a method and apparatus for determining the diffuse attenuation coefficient that can be used at depths to avoid marine life.

Yet another object is to provide an apparatus and method for determining point spread and beam spread of radiance.

Still another object is to provide a method and apparatus for determining the diffuse attenuation coefficient which does not require synchronization of a transmitter with a receiver.

These and other objects, advantages and novel features of the invention will become apparent from the following detailed description of the invention when considered in conjunction with the accompanying drawings.

BRIEF DESCRIPTION OF THE DRAWINGS

The drawing shows an operational embodiment of the apparatus suspended from a surface vessel, it being understood that, optionally, each element could be appropriately buoyed and weighted to achieve substantially identically the same separations and orientations so long as the relative dispositions of the elements remain.

DESCRIPTION OF THE PREFERRED EMBODIMENT

Referring now to the drawing, a diffuse attenuation coefficient determination apparatus 10 is shown operationally deployed from a surface support vessel 11. Winches 12 and 13 play out and retrieve lines 14 and 15 which place instrumentation packages to be elaborated on below a predetermined distance beneath the surface, usually several scattering lengths of interest.

An omnidirectional light source 16 is coupled to line 15 and acts as a lambertian source. A strobe light or other highly intense pulsed incoherent light source is acceptable so long as it radiates many joules of energy per pulse. The light source is offset from the vertically supported cable by a length 17 so that the supporting cable will not shadow or otherwise interfere with the pulsed light. Preferably, the offset length 17 is sufficient so that the cosine pulsed source is placed substantially in line with a cosine irradiance receiver 18 suspended from line 14 coming from winch 12.

The cosine receiver is oriented to face downwardly toward the pulsating light source. A horizontally extending mask 19 having an opening 19a further shields the downwardly facing receiver from other light sources, for example, surface ripples or waves reflecting ambient sunlight.

In a modified form a cosine receiver 18a, also provided with a mask 19a is mounted on supporting cable 15 above the source by a length 15a and offset a measured separation 15b. A displaceable unit 20 provides for changing the location of the receiver with respect to the source as the circumstances or data gathering needs demand.

Referring once again to the drawing, a typical scattering length of interest is approximately 50 feet. Lowering the source a distance, of say, 200 feet below the surface and the receiver distance of 150 feet below the surface, allows a responsive determination of the diffuse attenuation coefficient when driving signals are transmitted to the source and received from the receiver and monitored by instrumentation on the support vessel. Alternately, the power source could be self-contained at the source and appropriate monitoring and recording packages could be carried at the downwardly facing receiver. A further option is to have several receivers at different depths to simultaneously give a number of readings.

A salient feature of this inventive concept resides in the receivers being able to determine the diffuse attenuation coefficient, K, irrespective of variations in the sequential pulses from the light source. Both of the downwardly facing receivers 18 and 18a are lowered into the ocean's depths and are separated a predetermined distance. The source 16 is positioned below the receiver's, the source is pulsed and K is determined from the two receivers.

Both of the receivers can be mounted on line 15, one above the other and each provided with a suitable offset (offset 15b is shown holding receiver 18a away from line 15, it being understood a similar arrangement would be provided for receiver 18). The receivers are disposed such that there is no shadowing or other light interference.

All the instrumentation in the source and receivers are well known and common in the art. One design or another would be routinely selected and appropriately interconnected to provide responsive readings. Suitable pressure housings, heavy duty construction and rigging would be supplied.

While the suspension of the source and receivers from a surface vessel has been depicted in the drawings, it is well within the teachings of this inventive concept to have such an arrangement suspended from a submersible. It is also within the scope of this inventive concept to have proper buoyancy and anchoring attached to the receivers and the source to allow a moored or submersible carried disposition under the water surface. The latter approach may be more desirable in areas of heavy shipping or other reasons. Irrespective what deployment scheme is selected, it is essential that the downward facing orientation of the receivers be maintained. The relative location of the transmitter and the inclusion of the masking plate are also important. Locating the source below the downwardly facing receivers eliminates the possibility of outside sources' interfering with a determination of the diffuse attenuation coefficient. The lines feeding power to and signals from the source and receivers are kept aside from the light path to avoid shadows or, optionally, the power sources and recorders are carried on the source and receiver. In either case, responsive readings near the surface to great depths easily are obtained.

Obviously many modifications and variations of the present invention are possible in the light of the above teachings. It is therefore to be understood that within the scope of the appended claims the invention may be practiced otherwise than as specifically described.

What is claimed is:

1. An apparatus for measuring the diffuse attenuation coefficient of seawater during both day and night comprising:
    a pulsed cosine emitter source disposed below the water's surface several scattering lengths of interest for emitting pulsed light;
    a cosine response irradiance receiver interposed between the pulsed light emitting means and the water's surface being spaced from the pulsed cosine emitter source at least one scattering length of interest and facing downward for receiving irradiance from the pulsed light emitting cosine emitter source to generate responsive signals; and
    a length of line coupled to the pulsed light emitting means and the irradiance receiving means for separating them a a scattering length of interest equal to fifty feet.

2. An apparatus according to claim 1 further including:

means mounted on the irradiance receiving means for masking light from other than the pulsed light emitting means.

3. An apparatus according to claim 2 further including:
a length of line connected to the pulsed light omitting means and the irradiance receiving means for locating them both several scattering lengths of interest beneath the water's surface.

4. An apparatus according to claim 3 further including: at least a pair of cosine response irradiance receivers each downwardly facing and vertically separated from one another for determining the diffuse attenuation coefficient irrespective of variations in the light emitting means.

5. A method for measuring the diffuse attenuation coefficient of seawater across fifty foot scattering lengths of interest during both day and night comprising:
placing a pulsing light source several scattering lengths of interest beneath the water's surface;
locating an irradiance receiver that generates signals representative of pulsing light from the pulsing light source and located at least one scattering length of interest from the pulsing light source and below the water's surface;
facing the irradiance receiver downward toward the pulsing light source; and
monitoring the representative signals to provide a diffuse attenuation coefficient.

6. A method according to claim 5 further including:
separating the pulsed light source and irradiance receiver several scattering lengths of interest below the surface.

7. A method according to claim 6 further including:
masking sources of light other than the pulsed light source from the irradiance receiver.

8. A method according to claim 7 further including:
lowering the separated pulsed light source and irradiance receiver at least one scattering length of interest below the surface.

9. A method according to claim 8 in which the step of lowering involves the winching of an optionally interconnected irradiance receiver and pulsed light source downward.

10. A method according to claim 9 further including:
vertically separating at least one scattering length of interest at least two downwardly facing cosine receivers for determining the attenuation coefficient.

* * * * *